(12) United States Patent
Leers et al.

(10) Patent No.: US 6,949,090 B1
(45) Date of Patent: Sep. 27, 2005

(54) POST URINATION DRIP COLLECTOR

(76) Inventors: Jody L. Leers, 23555 Bel Ridge Dr., Elkhart, IN (US) 46516; James Eslinger, 23555 Bel Ridge Dr., Elkhart, IN (US) 46516

( * ) Notice: Subject to any disclaimer, the term of this patent is extended or adjusted under 35 U.S.C. 154(b) by 0 days.

(21) Appl. No.: 10/633,427

(22) Filed: Aug. 4, 2003

(51) Int. Cl.[7] .............................................. A61F 13/15
(52) U.S. Cl. ...................................................... 604/386
(58) Field of Search .............................. 604/353, 349, 604/346–347, 386; 128/885

(56) References Cited

U.S. PATENT DOCUMENTS

| | | | |
|---|---|---|---|
| 2,577,345 A * | 12/1951 | McEwen | 128/844 |
| 3,648,700 A * | 3/1972 | Warner | 128/844 |
| 4,601,716 A * | 7/1986 | Smith | 604/349 |
| 4,668,229 A * | 5/1987 | Fago et al. | 604/327 |
| 4,790,835 A * | 12/1988 | Elias | 604/349 |
| 4,863,448 A * | 9/1989 | Berg | 604/349 |
| 5,074,853 A * | 12/1991 | Bryant | 604/349 |
| D323,032 S | 1/1992 | McCrary | |
| 5,643,235 A * | 7/1997 | Figuerido | 604/352 |
| 6,129,719 A | 10/2000 | Nozaki et al. | |
| 6,416,500 B1 | 7/2002 | Wada et al. | |

* cited by examiner

*Primary Examiner*—Larry I. Schwartz
*Assistant Examiner*—Ginger Chapman

(57) ABSTRACT

A post urination drip collector includes a tubular member having a first end, a second end and a perimeter wall extending between the first and second ends. The first and second ends are open. A cap member is integrally coupled to and covers the second end such that a housing is defined. An absorbent material is attached to and substantially covers an inner surface of the cap member. The housing is removably positioned over a penis to collect any post urination dripping that may occur.

4 Claims, 1 Drawing Sheet

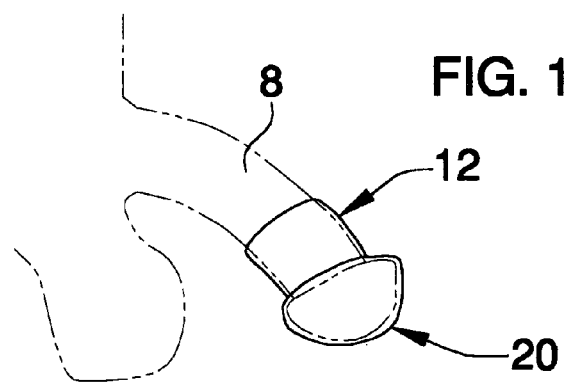
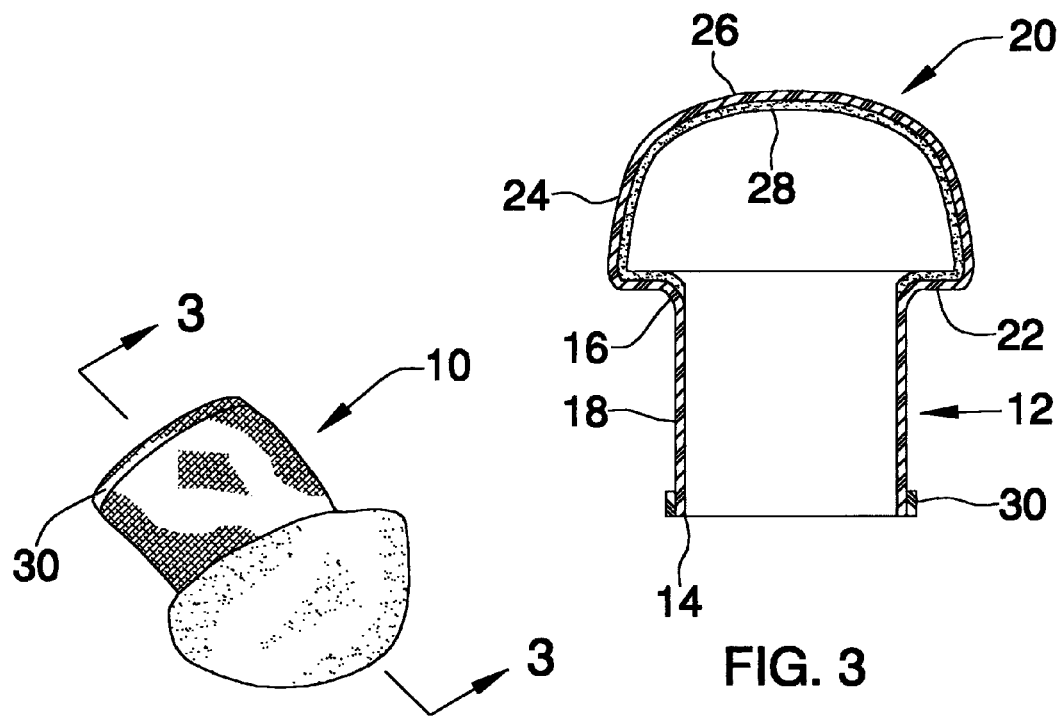

POST URINATION DRIP COLLECTOR

BACKGROUND OF THE INVENTION

1. Field of the Invention

The present invention relates to urination collection devices and more particularly pertains to a new urination collection device for the collection of post urination dripping.

2. Description of the Prior Art

The use of urination collection devices is known in the prior art. However, a primary flaw in these devices has been their ability to sufficiently retain themselves on a penis for a sufficient duration so that all urine expelled is caught. Therefore, the need remains for a device that retains itself on the penis in such a manner that it is generally only removed by the intended actions of the user to do such.

SUMMARY OF THE INVENTION

The present invention meets the needs presented above by using a housing that is positioned on the shaft of a penis and a cap member which is positioned on the head of the penis.

Another object of the present invention is to provide a new urination collection device that utilized an elastic band to further ensure that the housing remains on the penis.

Still another object of the present invention is to provide a new urination collection device wherein the cap member is generally shaped like the head of a penis.

To this end, the present invention generally comprises a tubular member having a first end, a second end and a perimeter wall extending between the first and second ends. The first and second ends are open. A cap member is integrally coupled to and covers the second end such that a housing is defined. An absorbent material is attached to and substantially covers an inner surface of the cap member. The housing is removably positioned over a penis to collect any post urination dripping that may occur.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a schematic side in-use view of a post urination drip collector according to the present invention.

FIG. 2 is a schematic side view of the present invention.

FIG. 3 is a schematic cross-sectional view taken alone line 3—3 of FIG. 2 of the present invention.

DESCRIPTION OF THE PREFERRED EMBODIMENT

With reference now to the drawings, and in particular to FIGS. 1 through 3 thereof, a new urination collection device embodying the principles and concepts of the present invention and generally designated by the reference numeral 10 will be described.

As best illustrated in FIGS. 1 through 3, the post urination drip collector 10 generally comprises a tubular member 12 having a first end 14, a second end 16 and a perimeter wall 18 extending between the first 14 and second 16 ends. The first 14 and second 16 ends are open. A cap member 20 is integrally coupled to and covers the second end 16 such that a housing is defined. Preferably, the housing comprises an elastomeric material.

In order to form a better fit on a penis, it is preferred that the cap member 20 has the shape of a penis head and includes a peripheral lip 22 that is integrally coupled to and extends outwardly away from the second end 16. A peripheral wall 24 is integrally coupled to and extends away from an outer edge of the peripheral lip 22. An end wall 26 is integrally attached to and extends along a length of the peripheral wall 24. The end wall 26 is preferably convex shaped.

Ideally, an absorbent material 28 is attached to and substantially covers an inner surface of the cap member 20. The absorbent material 28 may comprise any natural or synthetic absorbent material, however it is preferred that the absorbent material 28 comprises a cotton material.

An elastic band 30 is attached to and extends around an outer surface of the tubular member 12. The elastic band 30 is positioned generally adjacent to the first end 14.

In use, the device 10 is positioned over a penis 8, as shown in FIG. 1, after urination. The device 10 will absorb any post-urination dripping to ensure that urine does not stain or wet the user's clothing. After a self-determined amount of time, the device 10 may be removed or it may be retained in place until the next time the user of the device 10 urinates. It is preferred that a clean device 10 be used after each urination. Though the tubular member 12 and the cap member 20 are resiliently elastic, the elastic band 30 aids in ensuring that the device 10 does not inadvertently slip off of the penis 8.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A post urination drip collector device for removably positioning over a penis, said device comprising:

a tubular member having a first end, a second end and a perimeter wall extending between said first and second ends, said first and second ends being open, a cap member being integrally coupled to and covering said second end such that a housing is defined, said cap member including a peripheral lip being integrally coupled to and extending outwardly away from said second end, said lip being orientated generally perpendicular to said perimeter wall, a peripheral wall being integrally coupled to and extending away from an outer edge of said peripheral lip, an end wall being integrally attached to and extending along a length of said peripheral wall;

an elastic band being attached to and extending around an outer surface of said tubular member, said elastic band being positioned generally adjacent to said first end, said band being continuous and having a substantially rectangular cross-section; said elastic band being formed as a distinct member and an absorbent material being attached to and substantially covering an inner surface of said cap member.

2. The device of claim 1, wherein said housing comprises an elastomeric material.

3. The device of claim 1, wherein said absorbent material comprises a cotton material.

4. A post urination drip collector device for removably positioning over a penis, said device comprising:

a tubular member having a first end, a second end and a perimeter wall extending between said first and second ends, said first and second ends being open, a cap member being integrally coupled to and covering said second end such that a housing is defined, said housing comprising an elastomeric material, said cap member including;

a peripheral lip being integrally coupled to and extending outwardly away from said second end, a peripheral wall being integrally coupled to and extending away from an outer edge of said peripheral lip, an end wall being integrally attached to and extending along a length of said peripheral wall;

an absorbent material being attached to and substantially covering an inner surface of said cap member, said absorbent material comprising a cotton material; and an elastic band being attached to and extending around an outer surface of said tubular member, said elastic band being positioned generally adjacent to said first end, said band being continuous and having a substantially rectangular cross-section.

* * * * *